United States Patent [19]

Cupples et al.

[11] 4,032,591

[45] June 28, 1977

[54] PREPARATION OF ALPHA-OLEFIN OLIGOMER SYNTHETIC LUBRICANT

[75] Inventors: Barrett L. Cupples, Franklin Township, Allegheny County; William J. Heilman, Allison Park, both of Pa.

[73] Assignee: Gulf Research & Development Company, Pittsburgh, Pa.

[22] Filed: Nov. 24, 1975

[21] Appl. No.: 634,624

[52] U.S. Cl. .............................. 260/683.65; 254/59; 260/676 R; 260/683.9
[51] Int. Cl.$^2$ ....................... C07C 5/24; C07C 5/18
[58] Field of Search ........... 260/676, 683.9, 683.65

[56] References Cited

UNITED STATES PATENTS

| | | | |
|---|---|---|---|
| 3,149,178 | 9/1964 | Hamilton et al. | 260/683.9 |
| 3,177,159 | 4/1965 | Rodgers et al. | 260/683.9 |
| 3,663,635 | 5/1972 | Lassau et al. | 260/683.9 |
| 3,682,823 | 8/1972 | Smith et al. | 260/683.9 |
| 3,749,752 | 7/1973 | Pollitzer et al. | 260/683.9 |
| 3,763,244 | 10/1973 | Shubkin | 260/683.9 |

*Primary Examiner*—C. Davis

[57] ABSTRACT

An alpha-olefin oligomer synthetic lubricant having an improved viscosity-volatility relationship is prepared from an alpha-olefin such as 1-decene.

6 Claims, No Drawings

PREPARATION OF ALPHA-OLEFIN OLIGOMER SYNTHETIC LUBRICANT

FIELD OF THE INVENTION

This invention relates to the preparation of a hydrogenated alpha-olefin oligomer lubricant from an alpha-olefin, such as 1-decene, and more particularly it relates to an alpha-olefin oligomer product comprising trimer, tetramer and/or pentamer having an improved viscosity-volatility relationship and a higher Viscosity Index.

DESCRIPTION OF THE PRIOR ART

U.S. Pat. No. 3,149,178 describes the preparation of a synthetic lubricant by the batch polymerization of alpha-olefins, including 1-decene, in a reactor using boron trifluoride together with a promoter such as boron trifluoride.decanol complex to produce dimer, trimer and a residual polymer fraction and the hydrogenation thereof.

U.S. Pat. Nos. 3,763,244 and 3,780,128 describe the batch oligomerization of 1-olefins, such as 1-decene, in a reaction vessel using an alcohol or water co-catalyst and boron trifluoride bubbled through the reaction liquid to provide a molar excess of the boron trifluoride. A product mixture of dimer, trimer, tetramer and higher oligomers is hydrogenated.

SUMMARY OF THE INVENTION

We have discovered that an oligomer product useful as a synthetic lubricant comprising trimer, tetramer, pentamer or a mixture of any of these oligomers can be prepared having an inproved volatility-viscosity relationship and improved viscosity index. Further, we have discovered that a special hydrogenation procedure causes the skeletal rearrangement of the oligomer to provide these improved properties.

Oligomers of certain 1-olefins, particularly 1-decene and mixtures of 1-decene with 1-octene and/or 1-dodecene are highly useful as base fluids for preparing lubricants, hydraulic fluids, transmission fluids, transformer fluids, and the like, generically described as functional fluids, by the use of appropriate additives. Alpha-olefins oligomers can, in some instances, also be used as functional fluids without the use of property modifying additives. Each functional fluid product and generally the base fluid from which it is prepared must conform with established viscosity and volatility specifications. These alpha-olefin oligomer products are conventionally prepared by the cationic polymerization of the 1-olefin using a Friedel-Crafts catalyst. The cationic reaction mechanism is well known and is reported in the literature. The oligomer product is then hydrogenated in a conventional manner to stabilize the oligomer against oxidation and degradation.

We have found that the cationic polymerization of an alpha-olefin such as 1-decene using boron trifluoride and a co-catalyst which complexes with boron trifluoride conveniently prepares an oligomer mixture including the trimer, tetramer, and pentamer having optimum long chain branching for optimum properties as a base fluid in accordance with the reported reaction mechanism. Dimer, which is also a component of the oligomer product, is generally removed for separate use as a functional fluid, particularly use as a transformer fluid, to avoid volatilization loss from functional fluids comprising the higher oligomers. Pentamer is also present in the crude oligomerization product in an amount generally less than about 15 weight percent with minor or trace amounts of higher oligomers sometimes present. Other Friedel-Crafts catalysts including aluminum chloride and the like are well known in the literature for use in preparing alpha-olefin oligomer synthetic lubricants.

The composition of the oligomer mixture that is obtained from the oligomerization reaction is generally not the composition that is required to meet the viscosity specifications for a desired functional fluid product. This requires the separation of the oligomer composition into one or more product fractions comprising a single oligomer or a mixture of oligomers depending on the particular need.

The alpha-olefin oligomer functional fluids are especially adapted for use in exceptionally rigorous conditions, such as use as a hydraulic fluid and engine lubricant in jet aircraft involving both very high temperatures and very low temperatures as well as subatmospheric pressure or general use in an arctic environment. A particular problem has involved the need to meet both the viscosity specifications and the volatility specifications in these rigorous applications. Thus, such specifications require a relatively low subzero ($-40°$ C.) viscosity which can be accomplished by reducing the average molecular weight of the oligomer product. But this reduction in the average molecular weight of the oligomer not only requires a much higher proportion of trimer in the oligomer product which is more difficult to obtain in high yield in the oligomerization reaction, but it also increases the volatility of the lubricant at the high operating temperatures.

We have discovered that the viscosity-volatility relationship of an alpha-olefin oligomer base fluid, as well as the functional fluid produced therefrom, can be substantially improved by causing a significant skeletal rearrangement in the oligomer. The rearrangement introduces a substantial quantity of methyl and ethyl groups onto the long branched chains of the trimer, tetramer and pentamer. We have also discovered that this rearrangement improves the viscosity index of the oligomer product. The skeletal rearrangement described herein is accomplished in a special hydrogenation procedure.

The isomerization of the carbon structure of hydrocarbons is known to be very difficult. Since the hydrogenation of aliphatic double bonds is a simple, exothermic reaction, it would not be expected that skeletal rearrangement would occur during a conventional, double bond hydrogenation procedure. Surprisingly, we have discovered that substantial skeletal rearrangement can be obtained with the formation of property improving methyl and ethyl structures in the oligomer molecules by utilizing a special procedure for accomplishing the hydrogenation. It is surprising that this small chain branching, superimposed on the long chain branches of the oligomer, would produce the substantial improvement in the volatility-viscosity relationship and viscosity index which we have observed. It is also surprising that we are able to accomplish this small chain branching by skeletal rearrangement without also isomerizing the long branches to a more linear structure or without cracking the oligomer.

In our hydrogenation procedure, liquid oligomer at an elevated temperature is flowed or trickled over the surface of particles or pellets of the catalyst packed into a column in the presence of hydrogen at elevated pressure. This procedure involves an exceptionally intimate contact of the total liquid oligomer with the catalyst for a substantial period of time, since substantially all of the oligomer is present as a thin liquid film on the catalyst as the oligomer passes through the column. In this trickle-through procedure the great bulk of liquid oligomer is located on the catalyst surface with hydrogen gas predominating in the interstitial spaces between the pellets. Therefore, there is no large bulk of liquid far removed from catalyst surface at any time during the hydrogenation reaction.

The hydrogenation is preferably carried out at an elevated temperature of between about 100° C. to about 300° C. and preferably between about 150° C. and about 220° C. and a hydrogen pressure between about 200 psi. and about 2,000 psi. or higher and preferably between about 300 psi. and about 1,000 psi. These temperature ranges refer to the average temperature in the hottest zone of the catalyst bed as determined by thermocouple probes in the bed. We believe that there may be many localized hot spots in the catalyst pores substantially higher in temperature than the above range where substantial reaction is taking place and which may be a source of the improved results of our procedure. The upper pressure is limited by the cost of high pressure operation. We have found that the amount of skeletal isomerization to methyl and ethyl groups tends to increase as the hydrogenation temperature and/or hydrogen pressure increases in the trickle-through hydrogenation procedure described herein.

The procedure described herein is particularly suitable in the preparation of the trimer, tetramer and/or pentamer of alpha-olefins selected from 1-octene, 1-decene and 1-dodecene and mixtures thereof having a 210° F. (98.9° C.) viscosity of between about three centistokes and about 10 centistokes and preferably between about three and one-half centistokes and about eight centistokes. The preferred alpha-olefin is 1-decene with up to 50 mol percent 1-octene or 1-dodecene or a mixture thereof and the most preferred is 1-decene itself. The terms alpha-olefin, 1-olefin, 1-decene and the like in general and as used herein refer to the normal or straight chain olefin.

The oligomer resulting from the cationic polymerization of an alpha-olefin and useful herein is a mixture of internal olefins having long branched chains and having the double bond randomly distributed in the oligomer molecule. It is surprising to us that the skeletal rearrangement described herein does not occur to any significant extent in an alpha-olefin itself such as the 1-olefin monomer or the vinylidene dimer thereof. We have found that the procedure described herein is particularly useful in increasing the average molecular weight required to make a base fluid, which is particularly advantageous since the trimer is ordinarily difficult to prepare in high yield. Thus, we find that by our procedure we can prepare an oligomer base fluid from 1-decene having a 210° F. (98.9° C.) viscosity between about 5.4 and about 6.6 cs., having less than about 2 percent dimer, a maximum trimer to tetramer weight ratio of about 1:1 and at least about 15 weight percent pentamer and higher.

As stated the oligomer product which is skeletally isomerized by our process herein is prepared by cationic polymerization using a suitable Friedel-Crafts catalyst. We prefer to use boron trifluoride in combination with a boron trifluoride complexed with a promoter or co-catalyst which forms a coordination compound with boron trifluoride which is catalytically active for the oligomerization reaction. Suitable co-catalysts are well known in the art and include the aliphatic alcohols having from one to about 10 carbon atoms, water, carboxylic acids and alkyl ethers having up to about 10 carbon atoms, and the like. The preferred oligomerization procedure utilizes the boron trifluoride complex together with free boron trifluoride for enhanced rate of reaction.

The hydrogenation is carried out in a column packed to a suitable height with a solid hydrogenation catalyst in uniformly shaped particle, granule or pellet form, preferably averaging between about 1.5 mm. and about 6 mm. in diameter most preferably between about 3 mm. and about 4 mm. to insure sufficient porosity in the catalyst bed and suitable catalyst surface area. The catalyst can be any metal suitable for olefin hydrogenation such as nickel, platinum, palladium, copper, Raney nickel and the like on a suitable support such as alumina, kieselguhr, charcoal and the like, and having a suitable particle size within the specified range. The flow-through hydrogenation reactor can be pressured with hydrogen to a suitable pressure but we find that temperature control of the exothermic hydrogenation reaction can be conveniently accomplished, in part, by the flow of hydrogen through the catalyst bed at the desired pressure. Although conventional hydrogenation procedures may introduce some methyl and ethyl groups into the oligomer structure by skeletal rearrangement, we have discovered that our method substantially increases the amount of the skeletal rearrangement. We have further discovered that this substantial presence of methyl and ethyl branching resulting from our trickle-through procedure results in an improved viscosity-volatility relationship and improved Viscosity Index.

DESCRIPTION OF PREFERRED EMBODIMENTS

A purified stream of 1-decene was oligomerized at a temperature of 40° C. using boron trifluoride under 50 psi. (3.52 Kg/cm$^2$) and n-butanol as the co-catalyst to a product comprising 20.2 percent monomer, 9.4 percent dimer, 44.7 percent trimer, 19.2 percent tetramer and 6.5 percent pentamer. This oligomer product stream was slowly fed into the top of a first hydrogenation unit containing ⅛ inch (3.2 mm.) diameter nickel on kieselguhr (Harshaw Ni-0104-1/8T) catalyst and was allowed to trickle or flow along the surface of the catalyst pellets. This reactor had an internal diameter of 7⅝ inches (19.4 cm.) with the total depth of catalyst in the reactor being 78½ inches (199 cm.) and the catalyst volume being 15.5 gal. (58.7 l.). Hydrogen gas was flowed down through this reactor at an internal reactor pressure of 335 psi. (23.6 Kg/cm$^2$). The space velocity of oligomer product through the reactor was 5.5/hr.

The oligomer product was then trickled through a second hydrogenation reactor having an internal diameter of 11⅜ inches (28.9 cm.) and containing the same nickel on kieselguhr catalyst. This catalyst bed had a total thickness of 234 inches (5.95 m.) and a catalyst volume of 103 gal. (390 l.). The hydrogen was also flowed down through this reactor at an internal reactor pressure of 335 psi. (23.6 Kg/cm$^2$). The space velocity of the oligomer product through this second reactor was 0.7/hr. The average temperature in the first reactor was 199° C. and it was 202° C. in the second reactor. A light fraction was flashed off from the product from the second hydrogenation unit leaving a bottoms fraction having a 210° F. (98.9° C.) viscosity of 6.03 cs. suitable as a motor oil base fluid. This product is compared in Table I with a conventional hydrogenated motor oil base fluid prepared from 1-decene and having a 210° F. (98.9° C.) viscosity of 5.85 cs.

Table I

|  | Trickle Hydrogenation | Conventional |
|---|---|---|
| Viscosity, cs.[1] |  |  |
| −40° F. (−40° C.) | 7564 | 7830 |
| 0° F. (−17.8° C.) | 833 | 833 |
| 100° F. (37.8° C.) | 33.76 | 32.83 |
| 210° F. (98.9° C.) | 6.03 | 5.85 |
| Viscosity Index[2] | 138 | 134 |
| Evaporation loss, wt.%[3] | 4.8 | 6.8 |
| Oligomer distribution, wt.%[4] |  |  |
| $C_{20}$ | 1.0 | 0.3 |
| $C_{30}$ | 33.3 | 54.1 |
| $C_{40}$ | 42.3 | 33.4 |
| $C_{50}$ | 23.4 | 12.2 |
| $C_{30}/C_{40}$ | 0.79 | 1.62 |
| Avg. Mol. wt. | 524 | 486 |

[1] ASTM D 445
[2] ASTM D 2270
[3] ASTM D 972
[4] By Gas Chromatography

It is noted that the motor oil base fluid prepared from an oligomer fraction by hydrogenation according to our procedure possesses a much higher proportion of the heavier oligomers and has a significantly lower volatility and higher Viscosity Index at a similar viscosity specification than the conventional product. The product prepared by our procedure and the conventional product was analyzed for skeletal isomerization using carbon-13 nuclear magnetic resonance spectroscopy by correlating the oligomer spectrum with its known long branch, branched chain structure according to the conventional cationic reaction mechanism using the Lindemann and Adams equation (Anal. Chem. 43, p. 1245; 1971). This analysis disclosed about 25 percent more one and two carbon branching in the oligomer product prepared by the trickle-through hydrogenation procedure. There was little indication of branching in three or four carbon branches. In varying hydrogenation conditions we have found that a hydrogen pressure of 600 psi. (42.2 Kg/cm$^2$) and a temperature of 200° C. in both reactors produced substantially more methyl and ethyl branching in an oligomer than when it was hydrogenated in the first reactor only at the same conditions and it produced somewhat higher branching than the hydrogenation in both reactors at 400 psi. (28.1 Kg./cm$^2$) and 225° C. Two reactors were used herein merely for convenience in order to reduce the individual column height.

According to this invention the viscosity-volatility relationship can be substantially improved, that is, for a given viscosity the volatility can be reduced by hydrogenating the alpha-olefin oligomer in accordance with the hydrogenation procedure described herein. Also a given oligomer product can be treated according to the described hydrogenation procedure and its viscosity can be significantly lowered. An additional advantage resides in the significant elevation of the viscosity index when the trickle-through hydrogenation procedure as described herein is utilized.

It is to be understood that the above disclosure is by way of specific example and that numerous modification and variations are available to those of ordinary skill in the art without departing from the true spirit and scope of the invention.

We claim:

1. The process for skeletally isomerizing a liquid alpha-olefin oligomer comprising the trimer, tetramer, pentamer or mixtures thereof of a normal 1-olefin selected from 1-octene, 1-decene, 1-dodecene or a mixture thereof prepared by the cationic oligomerization of said 1-olefin which comprises introducing the liquid alpha-olefin oligomer into the top of a column packed with pellets of a metallic hydrogenation catalyst in the presence of hydrogen at a pressure and a temperature suitable for hydrogenation and permitting the liquid oligomer to trickle through said catalyst bed over the surface of said catalyst, whereby the liquid is substantially present in said column as a thin film on said catalyst pellets.

2. The process in accordance with claim 1 in which said 1-olefin is 1-decene.

3. The process in accordance with claim 2 in which said catalyst has an average particle size between about 1.5 mm. and about 6 mm.

4. The process in accordance with claim 2 in which the contact time of said liquid oligomer with said catalyst is sufficient to substantially completely hydrogenate said oligomer.

5. The process in accordance with claim 2 in which the temperature is between about 100° C. and about 300° C.

6. The process in accordance with claim 2 in which the hydrogen pressure is between about 200 psi. and about 2,000 psi.

* * * * *

UNITED STATES PATENT AND TRADEMARK OFFICE
CERTIFICATE OF CORRECTION

PATENT NO. : 4,032,591

DATED : June 28, 1977

INVENTOR(S) : Barrett L. Cupples and William J. Heilman

It is certified that error appears in the above-identified patent and that said Letters Patent are hereby corrected as shown below:

Under INID Code [75] line 2, delete "Allegheny County;"
and insert --Westmoreland County;--.
line 3, after "Allison Park," add
--Allegheny County;--.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*